(12) United States Patent
Weir

(10) Patent No.: US 11,337,653 B2
(45) Date of Patent: May 24, 2022

(54) BIOMETRIC SENSOR MOUNT

(71) Applicant: LULULEMON ATHLETICA CANADA, INC., Ontario (CA)

(72) Inventor: Ross Weir, Norfolk (GB)

(73) Assignee: LULULEMON ATHLETICA CANADA, INC., Vancouver (CA)

( * ) Notice: Subject to any disclaimer, the term of this patent is extended or adjusted under 35 U.S.C. 154(b) by 0 days.

(21) Appl. No.: 17/050,721

(22) PCT Filed: Apr. 26, 2019

(86) PCT No.: PCT/CA2019/050543
§ 371 (c)(1),
(2) Date: Oct. 26, 2020

(87) PCT Pub. No.: WO2019/204941
PCT Pub. Date: Oct. 31, 2019

(65) Prior Publication Data
US 2021/0085251 A1    Mar. 25, 2021

Related U.S. Application Data

(60) Provisional application No. 62/663,574, filed on Apr. 27, 2018.

(51) Int. Cl.
*A61B 5/00* (2006.01)
*A61B 5/0205* (2006.01)

(52) U.S. Cl.
CPC .......... *A61B 5/6831* (2013.01); *A61B 5/0205* (2013.01); *A61B 5/6804* (2013.01);
(Continued)

(58) Field of Classification Search
CPC ............ A61B 5/6831; A61B 2562/164; A61B 5/6838; Y10T 24/13; Y10T 24/1397
(Continued)

(56) References Cited

U.S. PATENT DOCUMENTS

| 8,956,289 B2 | 2/2015 | Kitajima et al. |
| 9,082,025 B2 | 7/2015 | Fastert et al. |

(Continued)

FOREIGN PATENT DOCUMENTS

WO    WO-2017075703 A1 *  5/2017  ........... A61B 5/6804

OTHER PUBLICATIONS

International Search Report in Application No. PCT/CA2019/050543 dated Jun. 25, 2019.
(Continued)

*Primary Examiner* — Gary Jackson
*Assistant Examiner* — Zahed Kabir
(74) *Attorney, Agent, or Firm* — DLA Piper LLP (US)

(57) ABSTRACT

A sensor mount may include a flexible substrate that may be folded to form a flexible inner portion that may be arranged to face a wearer and a flexible outer portion that may be arranged to face away from the wearer. The flexible inner portion and the flexible outer portion may define a channel and may be configured to secure the sensor mount to an article of clothing. A belt may be connected to the flexible outer portion. The outer flexible portion may include two slits configured to receive the belt such that the belt may be attachable to the outer flexible portion of the flexible substrate. A sensor may be disposed on the flexible inner portion of the flexible substrate.

16 Claims, 24 Drawing Sheets

(52) U.S. Cl.
CPC ............... *A61B 2560/0443* (2013.01); *A61B 2562/0219* (2013.01); *A61B 2562/0271* (2013.01); *A61B 2562/164* (2013.01)

(58) Field of Classification Search
USPC ................................................ 24/3.12, 3.13
See application file for complete search history.

(56) References Cited

U.S. PATENT DOCUMENTS

| | | | |
|---|---|---|---|
| 9,846,829 | B2 | 12/2017 | Faster et al. |
| 10,296,819 | B2 | 5/2019 | Fastert et al. |
| 2005/0131288 | A1 | 6/2005 | Turner et al. |
| 2007/0123756 | A1 | 5/2007 | Kitajima et al. |
| 2008/0287769 | A1* | 11/2008 | Kurzweil ............. A61B 5/6823 600/388 |
| 2009/0306485 | A1* | 12/2009 | Bell ...................... A61B 5/282 600/301 |
| 2014/0094675 | A1 | 4/2014 | Luna et al. |
| 2014/0097944 | A1 | 4/2014 | Fastert et al. |
| 2015/0057506 | A1 | 2/2015 | Luna et al. |
| 2015/0216475 | A1 | 8/2015 | Luna et al. |
| 2015/0230756 | A1 | 8/2015 | Luna et al. |
| 2015/0282768 | A1 | 10/2015 | Luna et al. |
| 2015/0286913 | A1 | 10/2015 | Fastert et al. |
| 2015/0297145 | A1 | 10/2015 | Luna et al. |
| 2015/0359491 | A1 | 12/2015 | Luna et al. |
| 2016/0066857 | A1 | 3/2016 | Crawford et al. |
| 2016/0066858 | A1 | 3/2016 | Crawford et al. |
| 2016/0066859 | A1 | 3/2016 | Crawford et al. |
| 2016/0070339 | A1 | 3/2016 | Crawford et al. |
| 2016/0070393 | A1 | 3/2016 | Sharma et al. |
| 2016/0095527 | A1* | 4/2016 | Thng ...................... A61B 5/339 600/301 |
| 2016/0157779 | A1* | 6/2016 | Baxi ..................... A61B 5/6831 600/301 |
| 2016/0291637 | A1* | 10/2016 | Rondel ................... G06F 1/163 |
| 2017/0235341 | A1* | 8/2017 | Huitema ................ G04G 17/08 361/679.03 |
| 2018/0293472 | A1 | 10/2018 | Fastert et al. |
| 2019/0022400 | A1* | 1/2019 | Kumar ................ A61N 1/3904 |

OTHER PUBLICATIONS

Written Opinion in Application No. PCT/CA2019/050543 dated Jun. 25, 2019.

\* cited by examiner

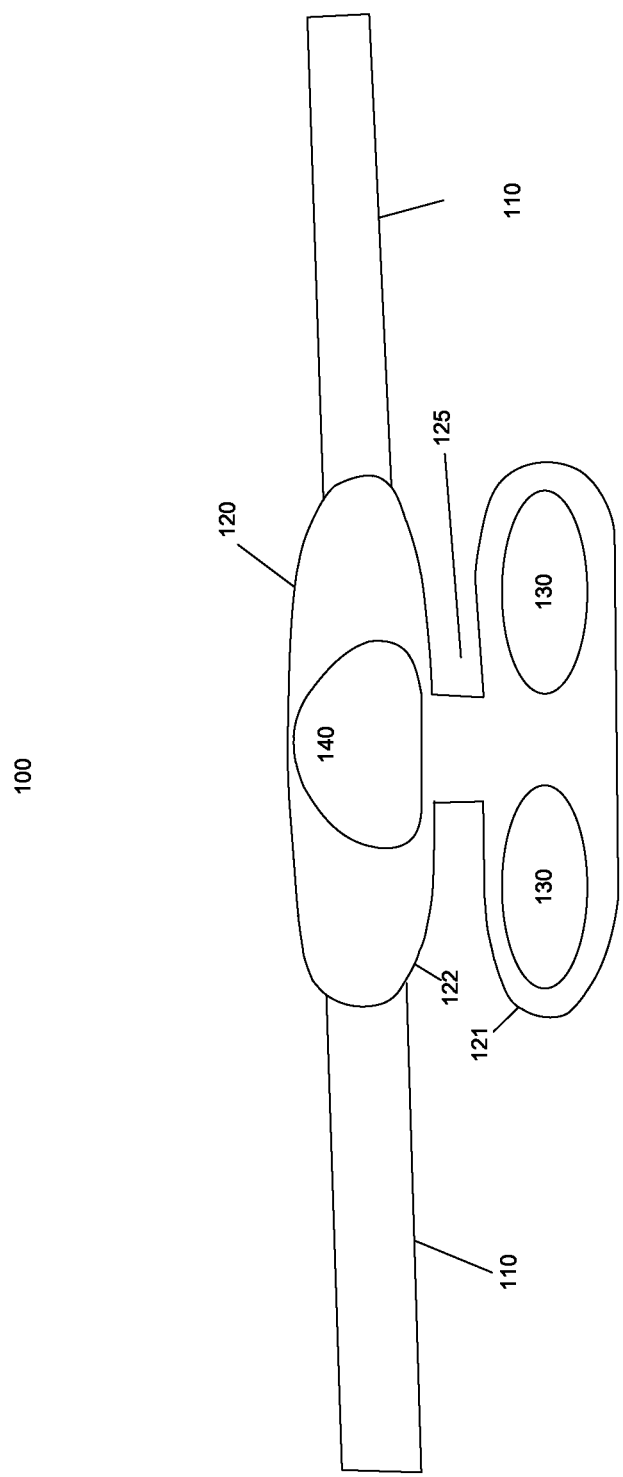

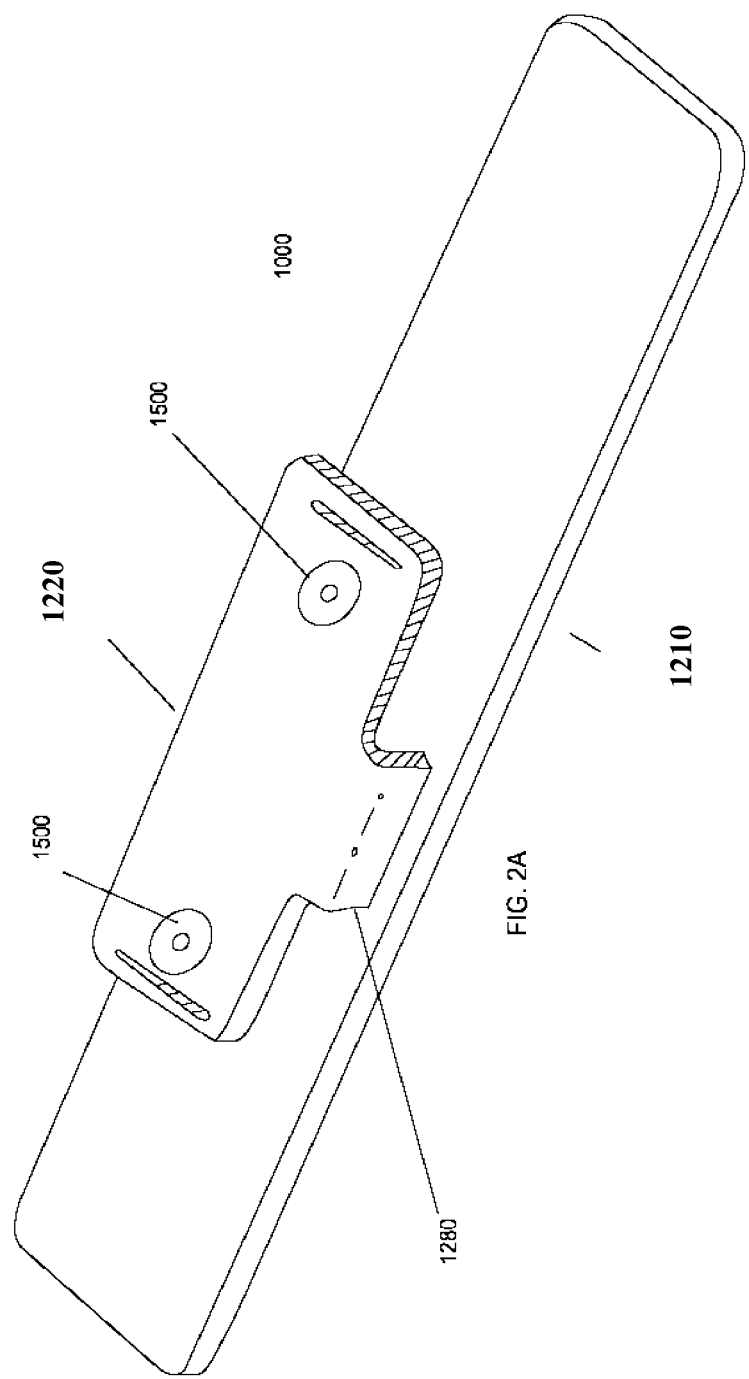

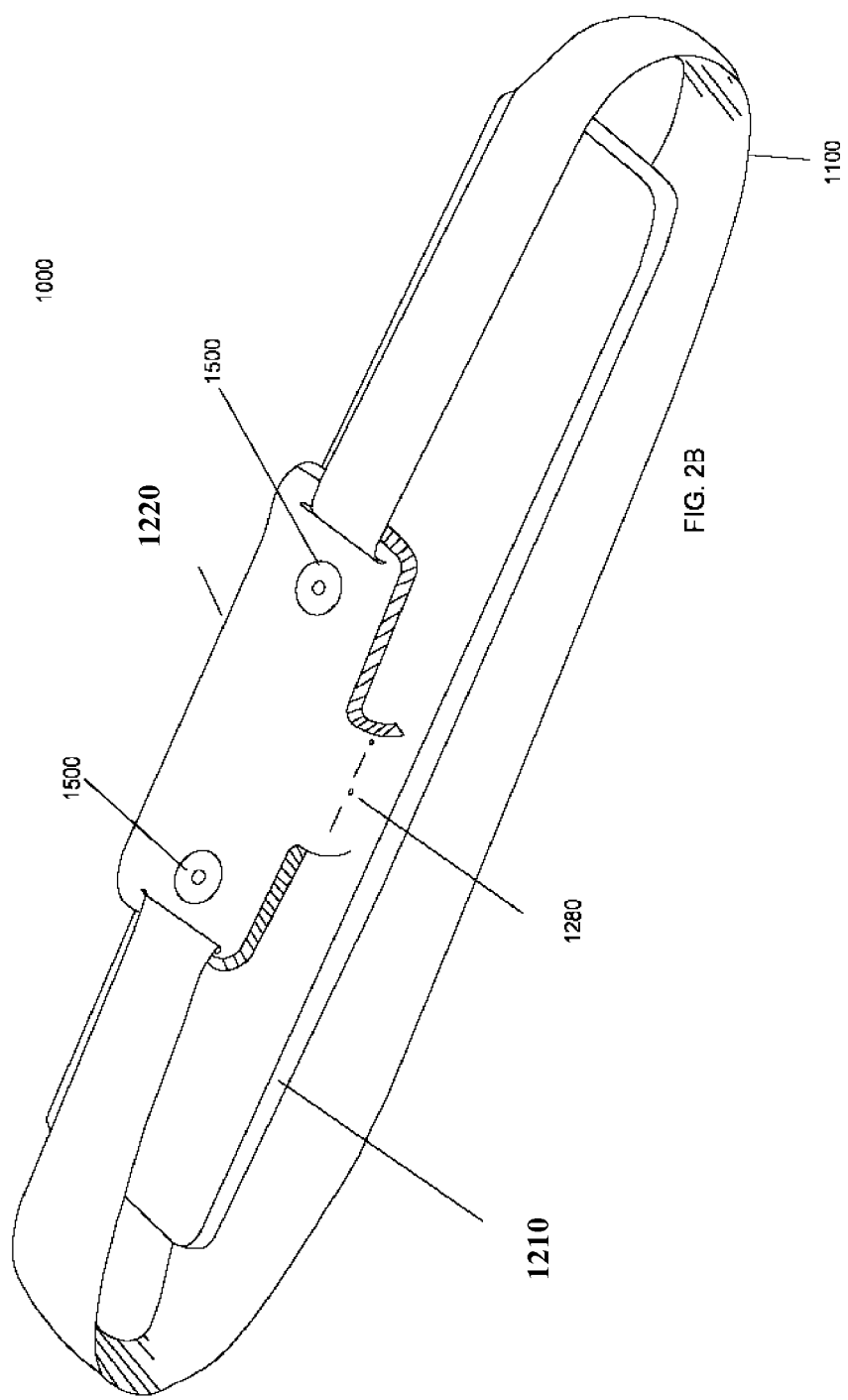

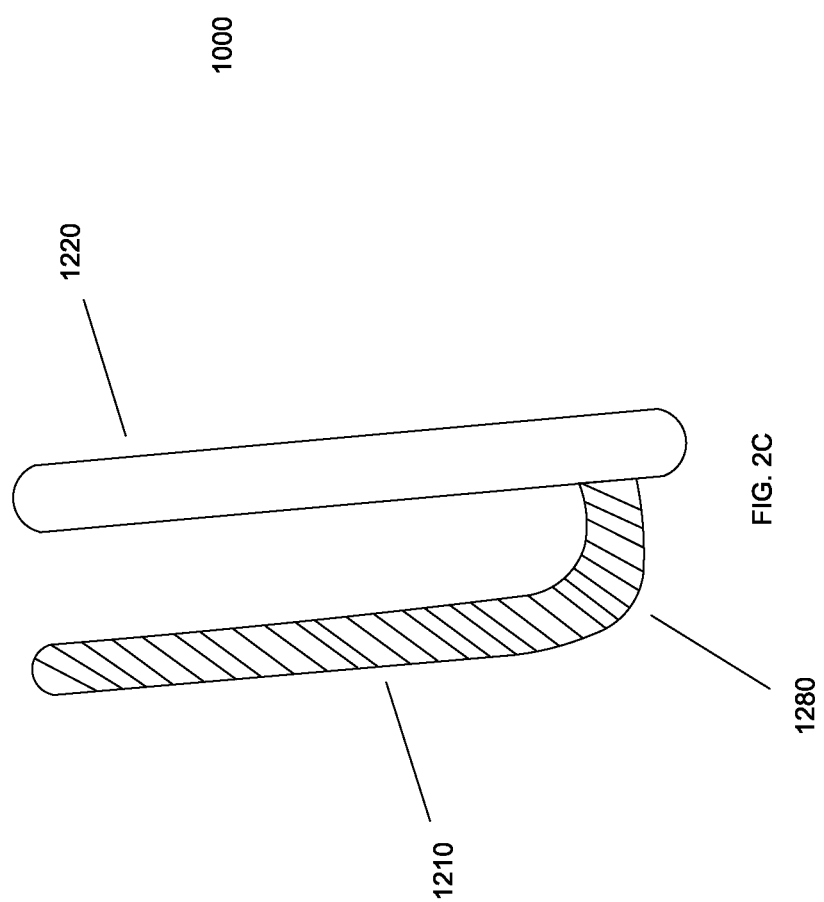

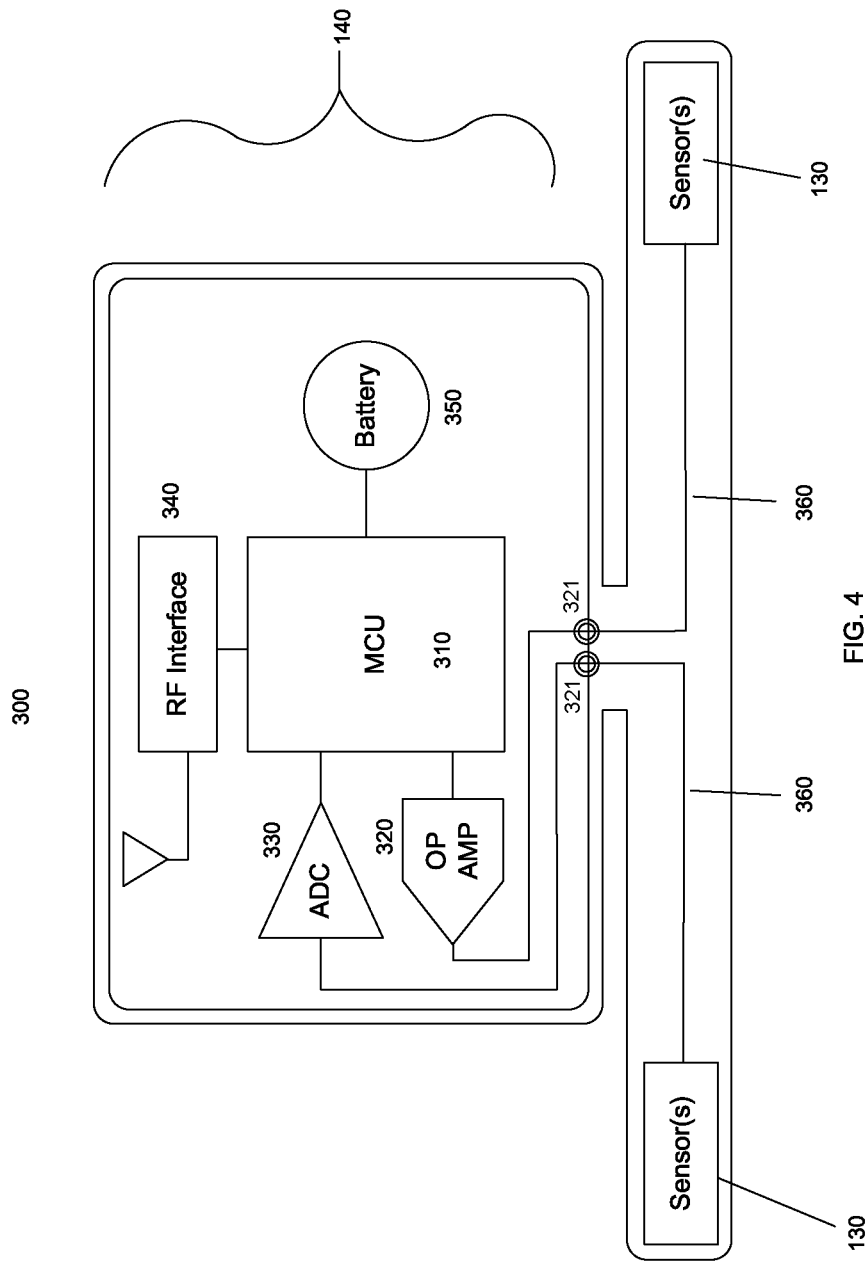

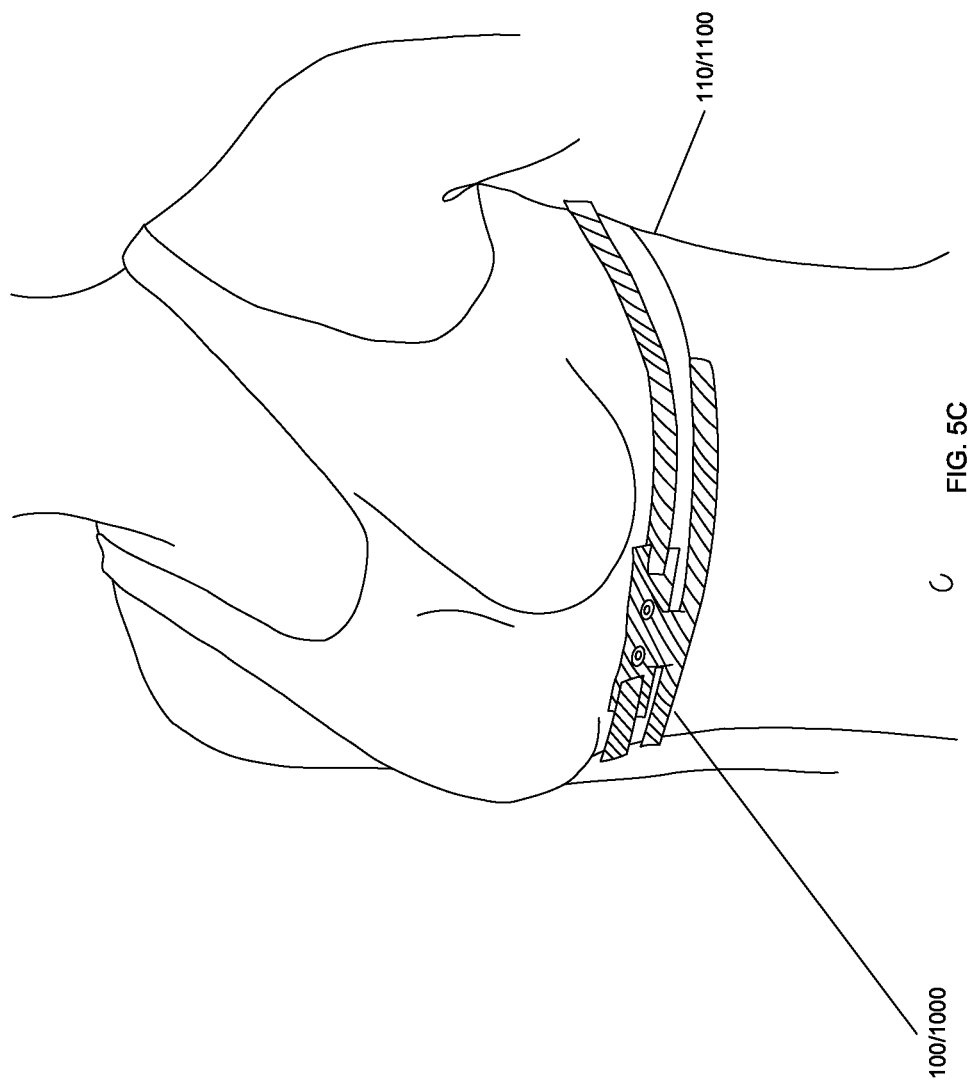

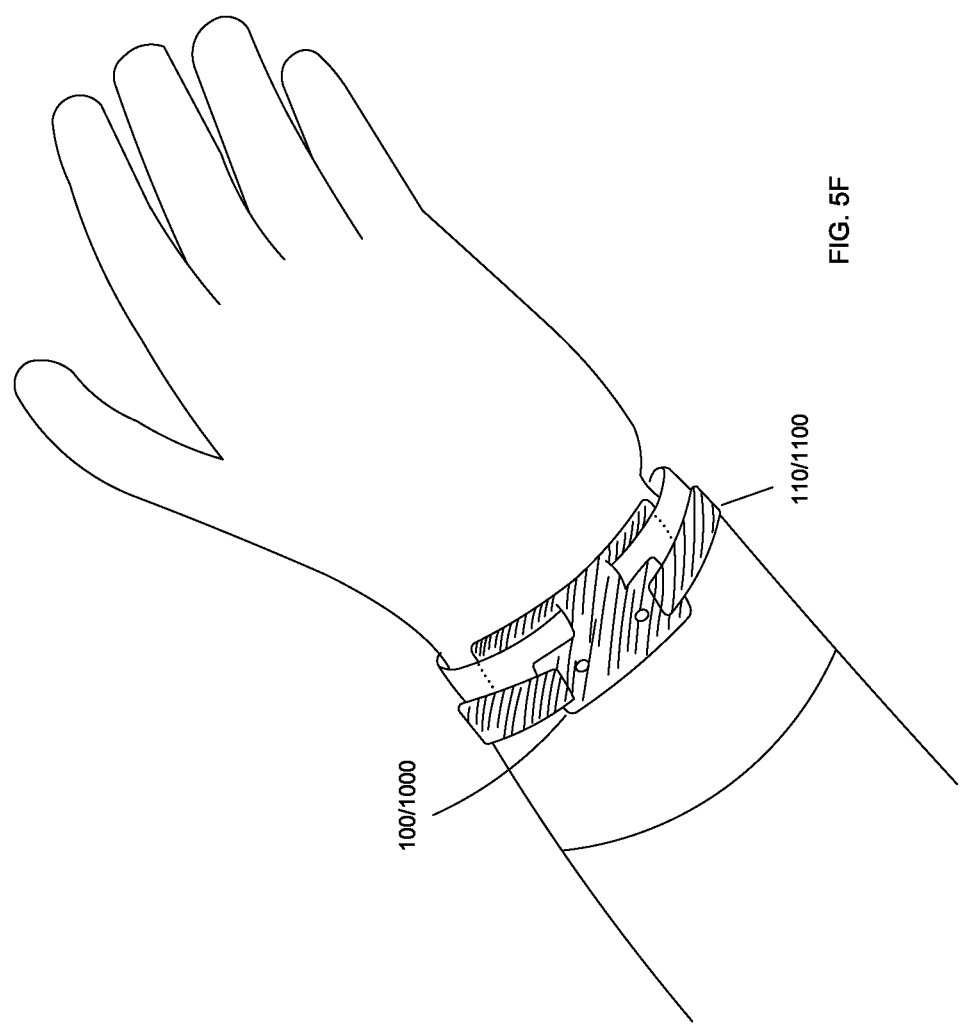

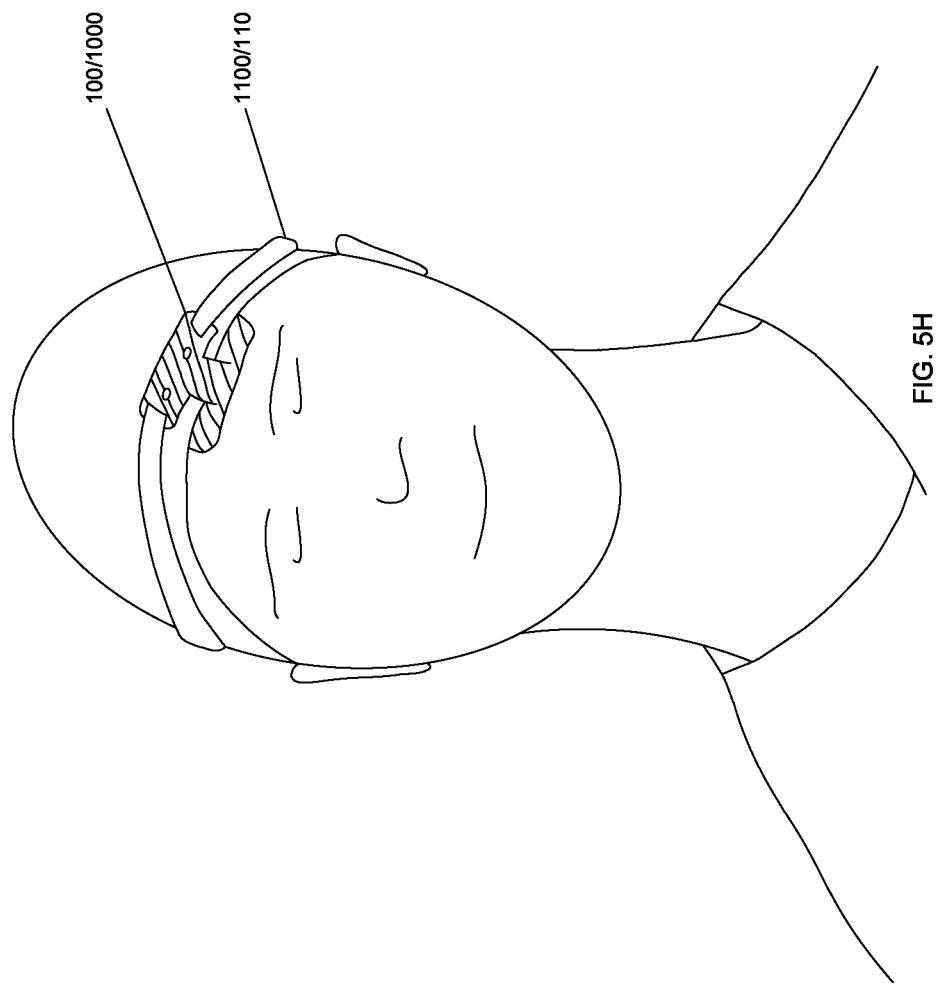

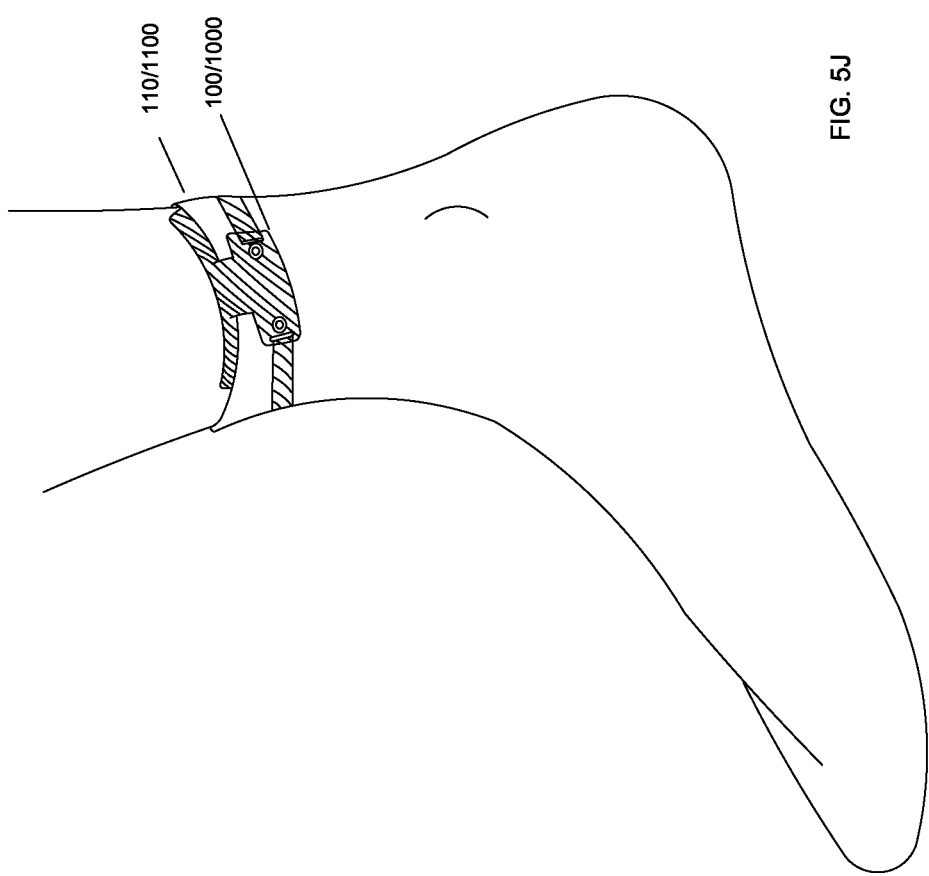

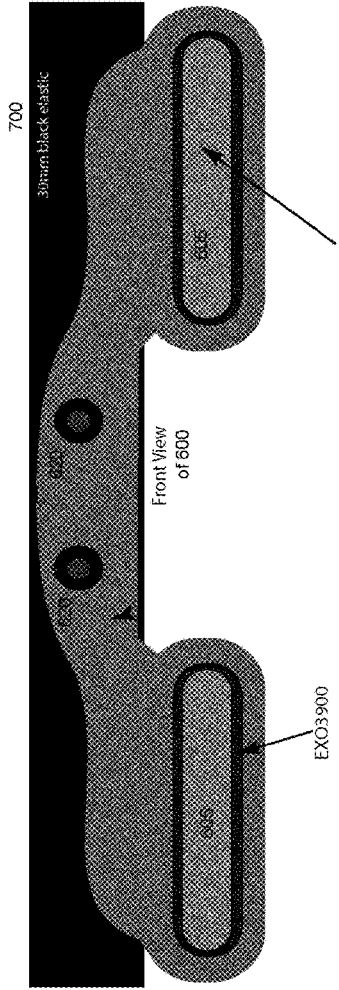

FIGURE 6B

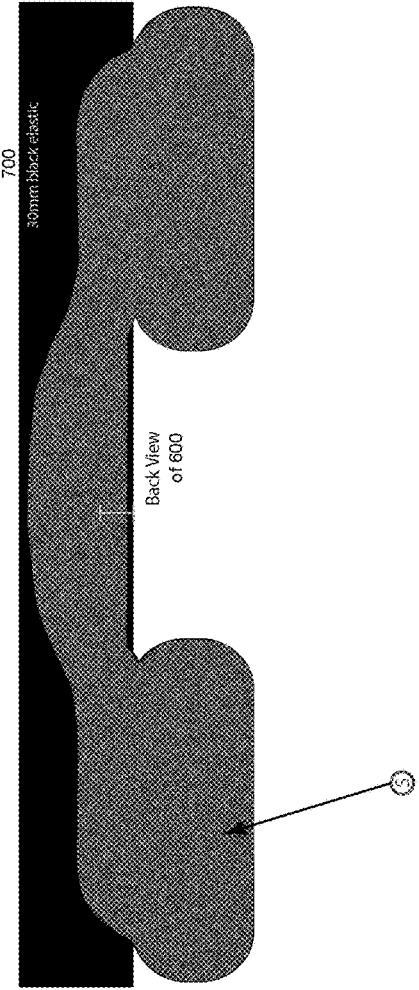

FABRIC
- S-(option 1) ULTRALU Black Lycra 295gsm/SP8027-1MFX5/Best Pacific
- S-(option 2) Light Ultralu Black Lycra 175gsm/EC10026 2MFX5/Best Pacific
- S-(option 3) self-fabric: Nulux Wicking 200gsm (Bright Lycra)/ DE070025/Trichel
- C1- conductive fabric/9372553/Noble Biomaterials, Inc.

TRIMS
- (elastic): EL24056/30/EL00137 - Stretch No Logo Dance Elastic - 30mm/Shanghai JML
- (D ring buckle) Prym Asia/article code TBD
- (Open buckle) Prym Asia/articld code TBD
- (Exoflex) EXO3900/Bemis
- (glue-TBD) 3415-6mil/Bemis
- (socket): Socket 4GB Stainless Steel P15193/Prym Asia
- (snap rubber washers) Prym Asia
- (logo)T00172 - 0.5mm Raised Matte Lulu Logo - 13mm | LUF201408071 (pocket opening)mobilon

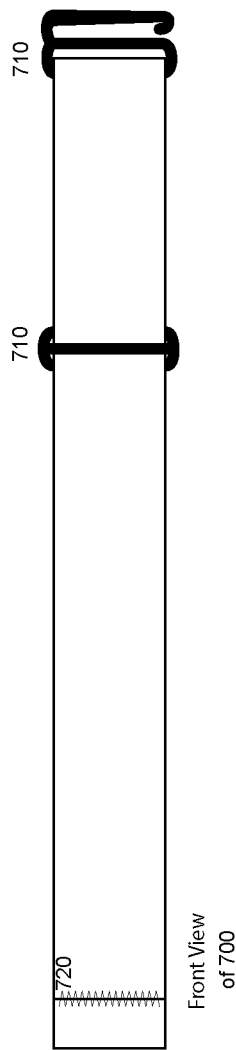
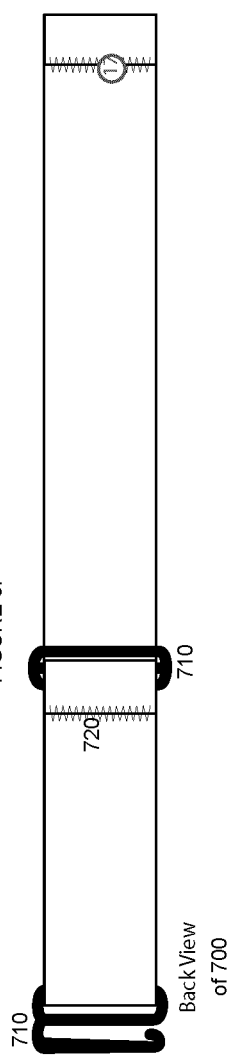

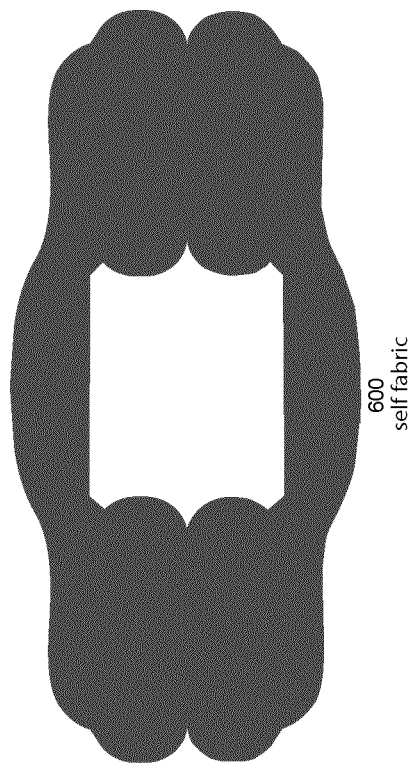
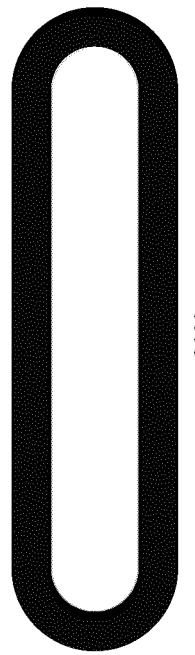
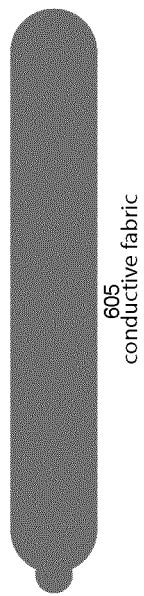

BIOMETRIC SENSOR MOUNT

CROSS REFERENCE TO RELATED APPLICATIONS

This application is a U.S. National Stage Application of International Application No. PCT/CA2019/050543 filed Apr. 26, 2019, which claims priority from U.S. Patent Application No. 62/663,574 filed Apr. 27, 2018. The entirety of all the above-listed applications are incorporated herein by their reference.

BRIEF DESCRIPTIONS OF THE DRAWINGS

FIG. 1A is a sensor mount with a strap according to an embodiment of the invention.

FIGS. 2A-2C are a sensor mount according to an embodiment of the invention.

FIG. 4 is a sensor mount circuit according to an embodiment of the invention.

FIGS. 5A-5K are sensor mounts worn at various places on a wearer's body according to embodiments of the invention.

DETAILED DESCRIPTION OF SEVERAL EMBODIMENTS

Figure 1B:
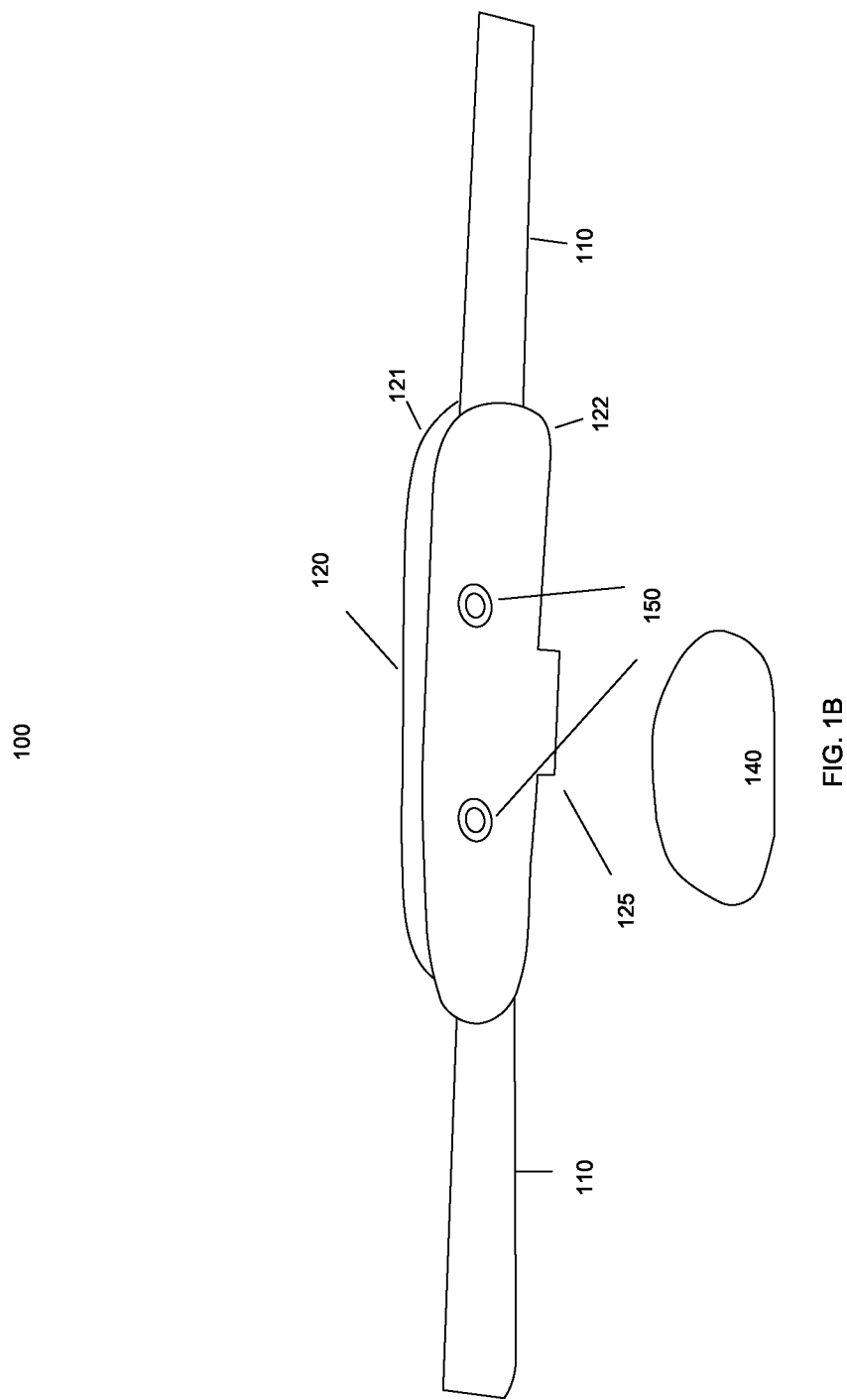
FIG. 1B is a sensor mount secured around a strap according to an embodiment of the invention.

Systems and methods described herein may provide mountings for biometric monitors and/or sensors. Biometric monitors may be used with sensors (e.g., electrodes) in sports and/or medicine for monitoring human biometric signals such as heart rate, skin temperature, galvanic skin resistance, etc. Some sensors may require contact with the skin, such as on the chest and close to the heart, on the wrist, etc.

In some embodiments, one or more sensors may be mounted in a sensor mount 100, such as the one illustrated in FIG. 1A. The sensor mount 100 may be a mounting mechanism that may be worn anywhere on the body, such as, but not limited to: an arm, a wrist, a leg, an ankle, a waist, a torso, etc. The sensor mount 100 may also be attached to and/or integrated with, for example, straps and/or belts. The sensor mount 100 may also be attached to and/or integrated with a piece of clothing and/or an accessory, such as, but not limited to: a bra, a shirt or other top, shorts, pants, socks, shoes, a hat, a watch, etc. The sensor mounts may include one or more sensors and one or more electronics units.

A sensor may be in, attached to, or on the sensor mount 100. Sensors may be made of, for example, conductive textiles, conductive polymers, conductive inks, and/or other materials. Some example sensors may include, for example, Smiths Medical™ 700 series thermistor skin temperature sensor, Smiths Medical™ Neo-Therm temperature sensor, Medline™ DYNJASK400SK skin probe with 400 series temperature sensor, Smiths Medical™ 700 series skin pressure sensor, QTC™ single point SP200 skin pressure sensor, NeuroAid™ carbon rubber electrode, Polar™ soft strap HR belt electrode, Texas Instruments™ TI ADXL345 acceleration sensor, Hamamatsu™ P12347-01CT optical sensor, Texas Instruments™ TI LMT70 air temperature sensor, Analogue Devices™ ADIS16266 microelectromechanical (MEMS) gyroscope, and/or others. Sensors may measure biometric signals (e.g., the electric pulse of the heart, skin temperature & humidity, galvanic skin resistance, brain activity, sweat chemistry, blood flow, blood oxygen levels & blood chemistry, body fat levels, etc.) and transmit measurement results to an electronics unit via one or more conductors connecting the sensor(s) and the electronics unit(s). Examples of an electronics unit (which includes a conductor) that may be used with the sensor mount 100 is a POLAR™ heart rate monitor, a GARMIN™ heart rate monitor, or a SUUNTO™ heart rate monitor, or others.

An example of a circuit comprising an electronics unit, a conductor, and sensors is illustrated in FIG. 4. In some embodiments, at least a portion of the circuit may be wireless (e.g., may comprise one or more wireless transceivers configured to wirelessly couple circuit elements to one another and/or to facilitate communication with other circuits). In some embodiments, the electronics unit may include a transmitter for transmitting an electric pulse as an analogous burst to a receiver and/or display unit such as a smart watch or smart phone. For example, the receiver and/or display unit may be a device worn at the wrist or a smart phone. As another example, the sensor mount itself may include hardware for storing and displaying the electric pulses, such as, for example, if the sensor mount 100 attached to the wrist. Electronic components included in the sensor mount 100, such as the electronics unit, the conductor, and the sensors, may be coated with a protective coating such as plastic or rubber or a thin film, for example, which may provide insulation against moisture penetration.

As mentioned previously, in some embodiments, the sensor mount 100 may be attached to and/or incorporated into articles of clothing. For example, sensor mount may attach to: a bra, a waist of pants or shorts, socks, etc. Other examples may include a sensor mount 100 that is incorporated into: a bra, a waist of pants or shorts, etc.

In some embodiments, a sensor in the sensor mount 100 may be held internal to the bra (e.g., facing the skin) with the electronics unit and/or the conductor (or part of the conductor) held external to the bra. In other embodiments, the sensor(s) may be held in the sensor mount 100 of FIGS. 1A and 1B, with the sensor mount 100 folded so that the sensor(s) are facing the skin and the electronics unit and/or the conductor (or part of the conductor) are facing away from the skin. In this manner, a wearer may feel less bulk due to the sensor mount 100 elements as only the sensors and the material of the sensor mount 100 are next to the skin, while the bulkier sensor mount elements (e.g., the electronics unit and/or the conductor (or part of the conductor) face away from the skin.

In some embodiments, the sensor mount 100 may be fold in a manner that is flexible, as shown in FIGS. 1A-1B. In other embodiments, the sensor mount 100 may be folded in a manner that is less flexible and akin to a clip such that the sensor mount 100 easily attaches and is held in place by the clothing (e.g., the bra, the shorts, the socks, etc.) as shown in FIGS. 2A-3B.

FIG. 1A illustrates details of a sensor mount 100, according to an embodiment of the invention. The sensor mount 100 may include a strap 110 and a substrate 120. The strap 110 may attach to and extend from each of a first and second end of the substrate 120. The strap 110 may be made of a flexible material, such as an elastic band or a knit fabric, for example nylon 6.6 spun into filaments, twisted into yarn with additional elastane yarns and knitted into a narrow width fabric. As shown in FIG. 1A, the strap 110 may be two pieces that connect to the substrate 120. The strap 110 may also be a single strap that wraps around a wearer's body. The strap 110 may be made of material such as: In addition, the strap 110 function may be performed by part of a bottom portion of any bra (e.g., the strap 110 may be the underband), as shown in FIG. 3. The substrate 120 may be made of a flexible material such as a knit or woven fabric, a nonwoven fabric, neoprene, an elastomeric film (e.g. thermoplastic polyurethane (TPU) film), any other flexible material, or any combination thereof. In some embodiments, the substrate 120 and/or the strap 100 may be made such that they conform to the shape of the wearer's body. In some embodiments, the substrate 120 may be sufficiently flexible to conform to a wearer's body even if the strap 100 is not flexible enough to conform to a wearer's body.

Some strap 110 embodiments may be made using one of two types of belt construction. The first type may include molding, for example from synthetic rubbers such as TPU, silicon, and/or polyvinyl chloride (PVC), which may have good properties for direct skin contact (soft, anti-allergy, etc.). The second type may include laminating, for example directly to narrow with elastics. The elastics themselves may be made from a number of different textile materials such as nylon, polyester, or a blend of the two. When the elastics are knitted, elastane, silicon, or similar materials may be included to allow for stretch recovery of the belt material. Other materials may be used, such as polypropylene, viscose, rayon, or natural fibers like wool or cotton.

In either case, the electrode material may be made from a high carbon content polymer to provide a conductive sensor capable of transducing electrical currents emitted by each heartbeat. The synthetic rubber may be a TPU formulation with the addition of carbon powder. Other material options for electrodes may include metallic coatings (e.g., silver or silver chloride) that may provide a conductive surface.

In laminating the thin and flexible electrodes to the belt material, a thermoplastic adhesive may be used. Such adhesives may be urethane based (e.g., Bemis adhesives-Flowfree films). Adhesives may be heat activated when all the parts are assembled correctly, providing a permanent bond between the layers.

As discussed in greater detail below, the electronics and battery may be contained in a separate module that can be either molded into the belt material or designed to clip on and off the belt. When clipping the module onto the belt, a number of clipping options may be available, such as a conductive pin and clip assembly that may allow the module to be press fit, secured, and pulled off as required. Such conductive push closures may be commonly used in the apparel industry and may be made from conductive metals such as steel.

One or more sensors 130 may be housed in the substrate 120 and arranged in a first part of the substrate 121 so that they contact the wearer's body when worn. Some sensors, such as acceleration and/or optical sensors, may not necessarily be placed in direct contact with the wearer's body, as they may be able to take accurate measurements without contact. Sensors may be made of, for example, conductive textiles, conductive polymers, conductive inks, and/or other materials. The sensors 130 may also be flexible and/or may be sized, shaped, and positioned to prevent wearer discomfort. An electronics unit 140 may be disposed on a second part 122 of the substrate 120 (e.g., see FIG. 4). The electronics unit 140 may include processing and/or monitoring elements which may receive signals from the sensors 130 via one or more conductors disposed in or on the substrate 120. Conductors may be made of conductive textiles, polymers, flexible circuit boards, or other flexible elements, for example. The substrate 120 may be foldable so that the sensors 130 may be placed in contact with the wearer's skin while the electronics unit 140 is folded down so that it is on the outside of the belt 100. In some embodiments, the electronics unit 140 may be separated from the sensors 130 by a flexible hinge 125. The hinge 125 may be an integral part of the substrate 120 or may be a separate element fastened to the substrate 120 and arranged to provide a physical and electrical connection between the separate portions of the substrate 120 containing the sensors 130 and the electronics unit 140, respectively. The substrate 120 may be folded around a belt or portion of a garment such that the bulk of the belt 100 is outside a bra or other garment with only the thin and/or flexible sensors 130 under the underband of the bra and/or on the inside of the garment. In some embodiments, the substrate 120 may not be foldable, but may instead be formed in a folded configuration such that the portion of the substrate 120 with the sensors 130 and the portion of the substrate 120 with the electronics unit 140 define a channel into which a belt 110 or garment may be inserted during wear.

The strap 110 may be manufactured by heat laminating layers of substrate fabric, conductive (textile or polymer) materials, and insulation layers together. A connector (e.g. a snap button) may be disposed on the strap 110 and may provide electrical connection between the separate portions of the substrate 120 in some embodiments. The strap 110 may comprise a length adjustment mechanism built by using hooks and slider components and sewing processes.

FIG. 1B illustrates the sensor belt 100 with the substrate 120 folded closed. In this arrangement, the first part 121 of the substrate 120 on which the sensors 130 are disposed may flex independently of the second part 122 of the substrate 120 on which the electronics unit 140 is disposed. This may allow the first part 121 of the substrate 120 to comfortably make contact with the wearer even if the size, bulk, and/or rigidity of the electronics unit 140 prevents or restricts flexing of the second part 122 of the substrate 120. The electronics unit 140 may be detachable from the substrate 120 and may attach to the substrate 120 by one or more connectors 150, which may include snap connectors or other suitable connectors (e.g., connectors found on SUUNTO™ comfort belts or UNDER ARMOUR™ belts). The connectors 150 may electrically connect the electronics unit 140 with the conductors that are connected to the sensors 130.

Figure 3A:
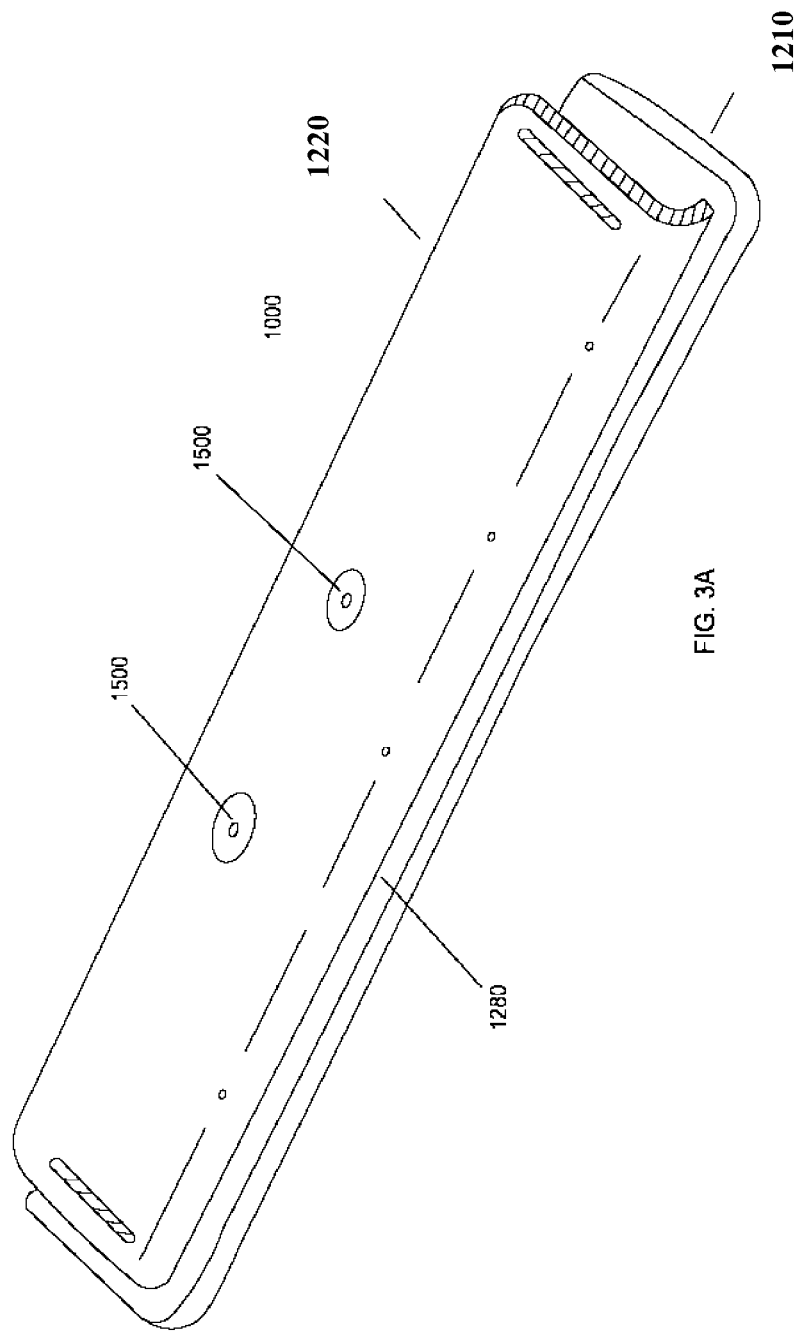
FIGS. 3A-3B are a sensor mount according to an embodiment of the invention.
Figure 3B:
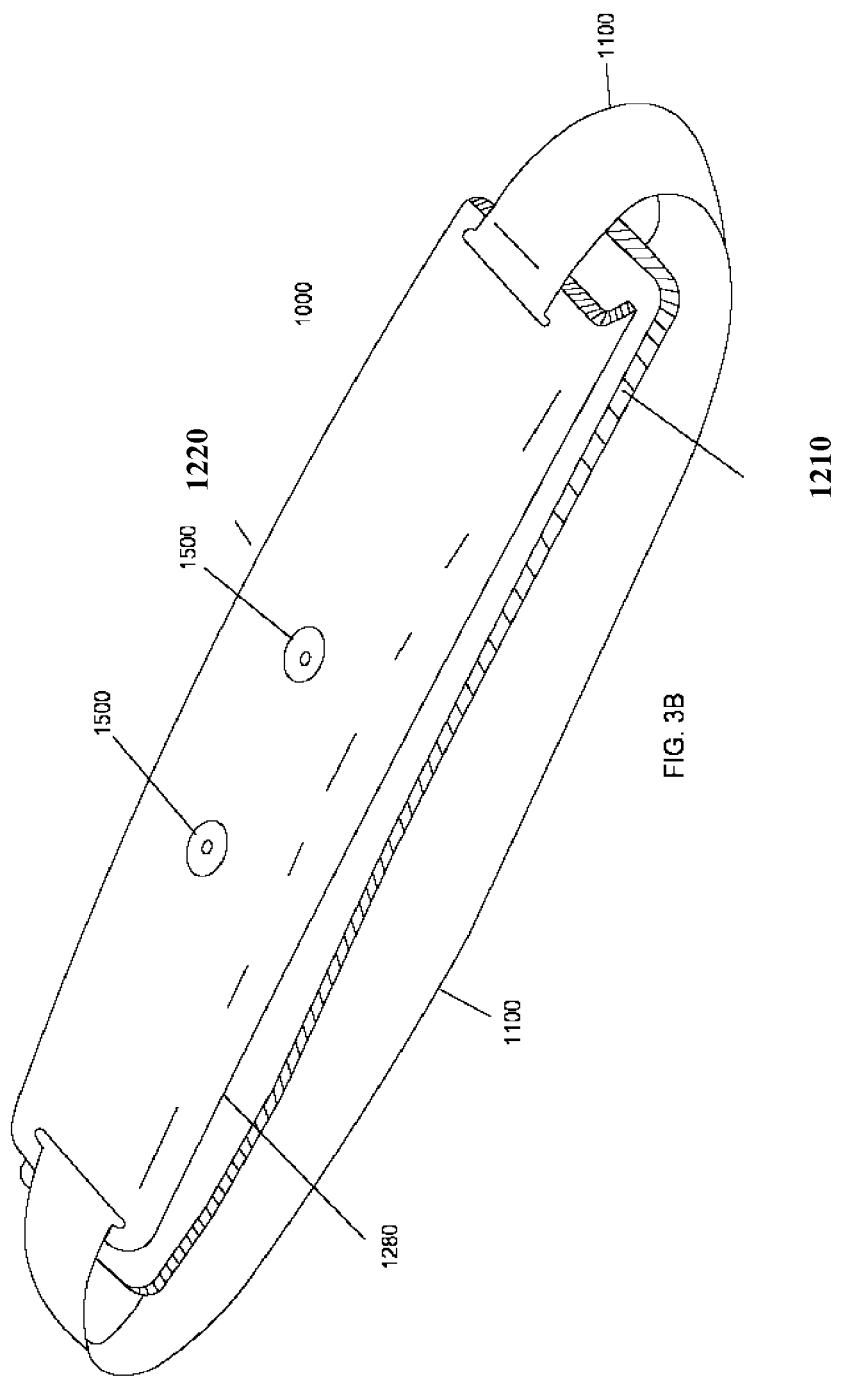

FIGS. 2A, 2B, and 2C illustrate details of a sensor mount 1000, according to an embodiment of the invention, which may be configured with a rigid or semi-rigid attachment 1280 instead of the hinge 125 of FIGS. 1A-1B. FIG. 2A shows the sensor mount 1000 without the strap 1100, FIG. 2B shows the sensor mount 1000 with the strap 1100, and FIG. 2C shows a side view. The internal components of the sensor mount 1000 of FIGS. 2A-2C may be the same as those of the sensor mount 100 of FIGS. 1A-1B. However, the attachment 1280 joining the first part 1210 of the substrate and the second part 1220 of the substrate may be rigid or semi-rigid, defining a channel in which the strap 1100 or an article of clothing may be disposed. One or more connectors 1500, which may include snap connectors or other suitable connectors (e.g., connectors found on SUUNTO™ comfort belts or UNDER ARMOUR™ belts), may electrically connect the electronics unit 140 with the conductors that are connected to the sensors 130. FIGS. 3A and 3B show an alternate embodiment of the sensor mount 1000 wherein the attachment 1280 spans the entire length of the first part 1210 of the substrate.

FIG. 4 is a sensor circuit 300 according to an embodiment of the invention. The electronics unit 140 may include a microprocessor or controller (MCU) 310 which may be coupled to the sensors 130 via an operational amplifier (OPAMP) 320 and/or analog to digital converter (ADC) 330. MCU 310 may be a Texas Instruments™ TI CC2640 or CC2540, with BLE Antenna, for example. OPAMP 320 may be provided by a Texas Instruments™ TI ADS1291 (a multichannel, simultaneous sampling, 24-bit, delta-sigma (ΔΣ) analog-to-digital converter (ADC) with a built-in programmable gain amplifier (PGA), internal reference, and an onboard oscillator), for example. OPAMP 320 and/or ADC 330 may couple to the sensors 130 via electrodes 360. A battery 350 or other power source (e.g., CR2032 coin battery and Texas Instruments™ TI BQ24040 charging circuit) may power the MCU 310 and other components. The MCU 310 may be coupled to a transceiver (e.g., RF interface, Bluetooth, etc.) 340 for sending and/or receiving data to and/or from an external display device such as a smart phone or smart watch. The external display device may display data gathered by the sensors 130 and processed by the MCU 310. For example, sensors 130 may gather user heart rate, temperature, etc. data. This data may be converted to a digital signal by ADC 330, processed by MCU 310, and output as biometric information to the display device via transceiver 340. Conductive snap buttons 321 may be used as shown in FIG. 4.

Figure 5A:
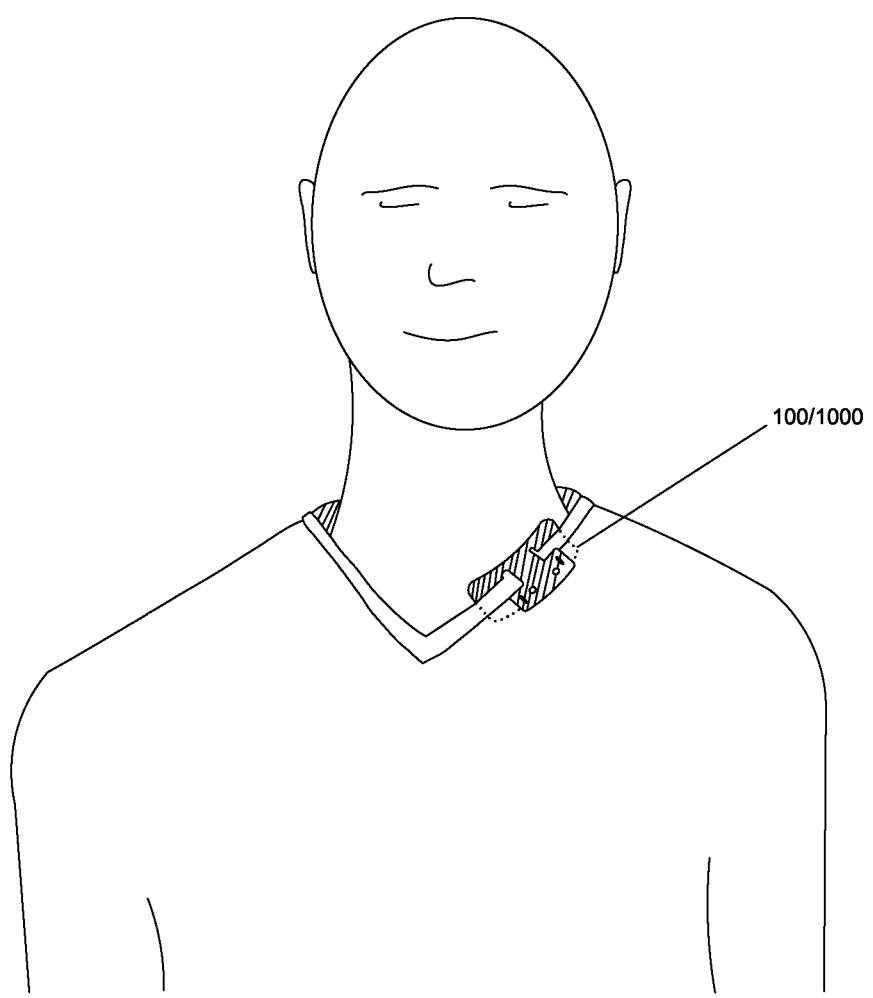
Figure 5B:
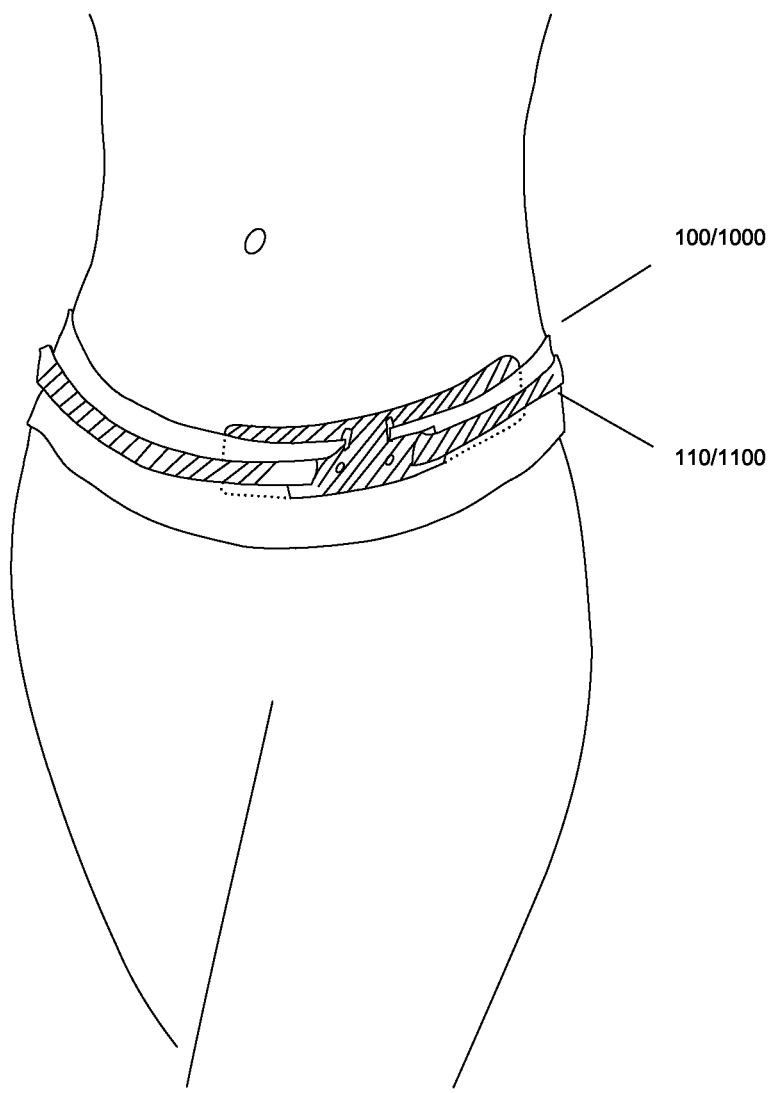
Figure 5D:
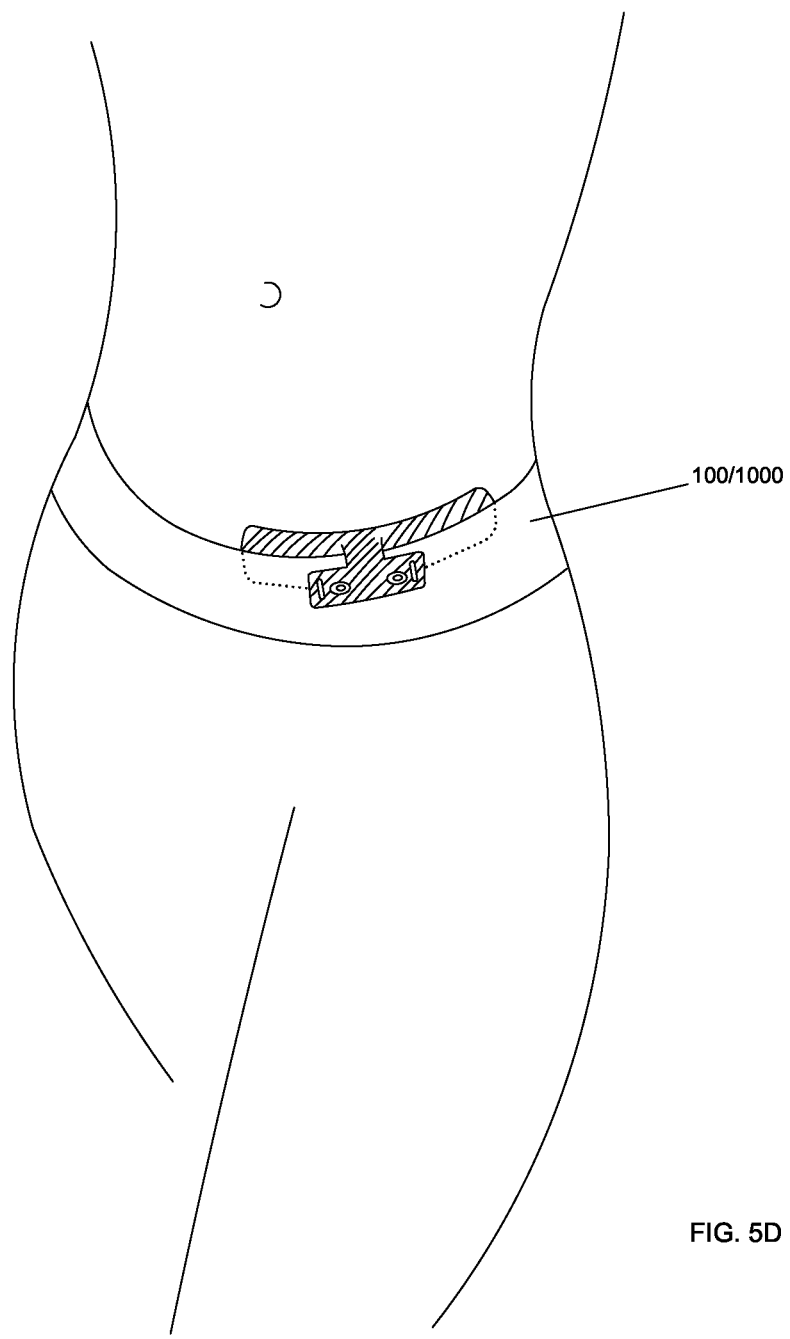
Figure 5E:
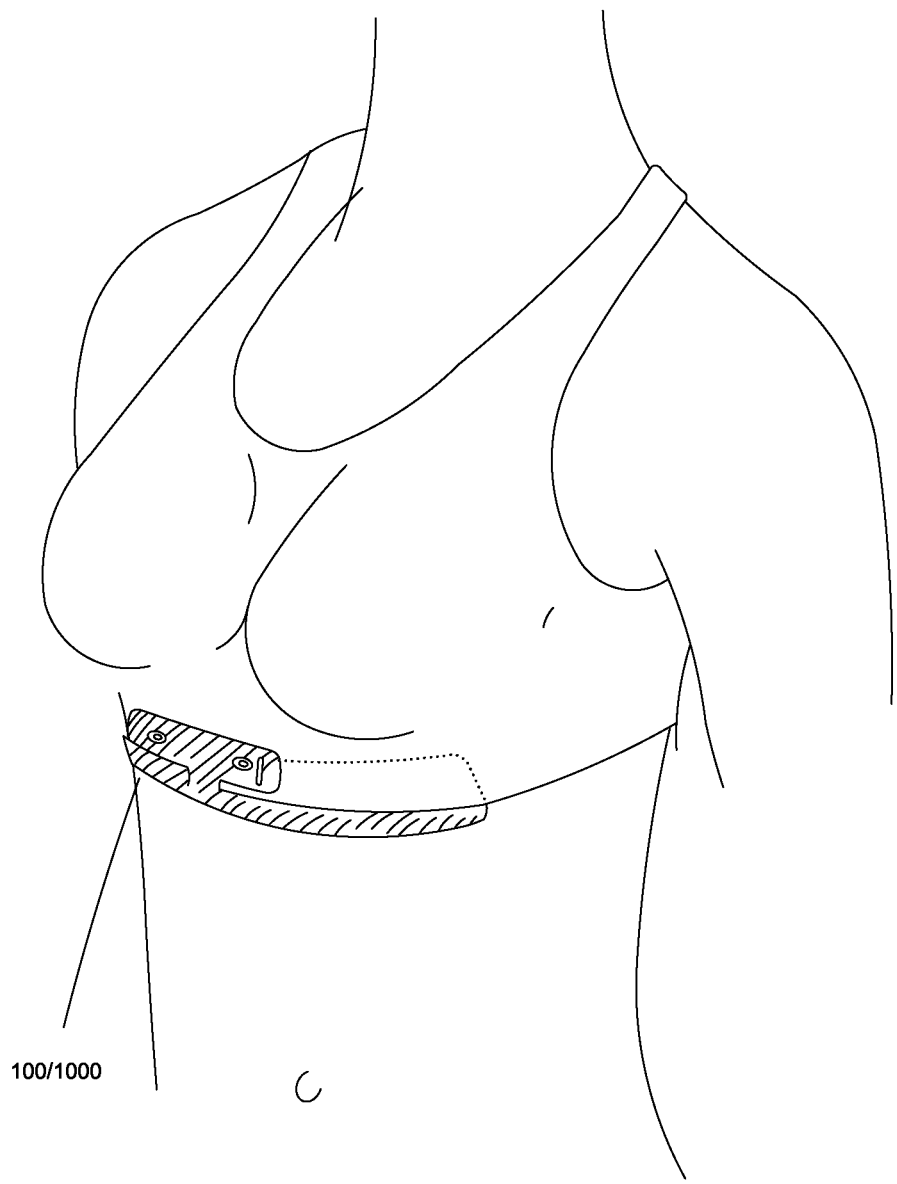
Figure 5G:
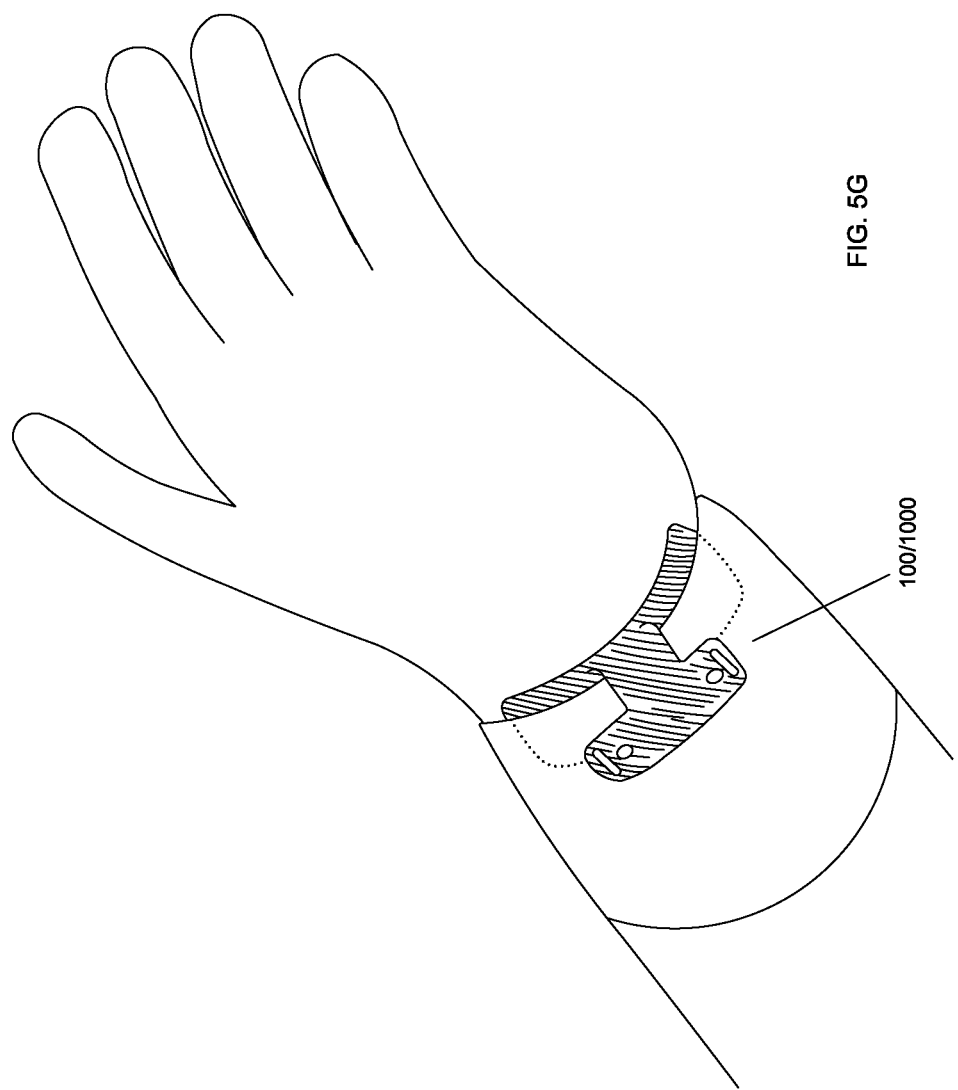
Figure 5I:
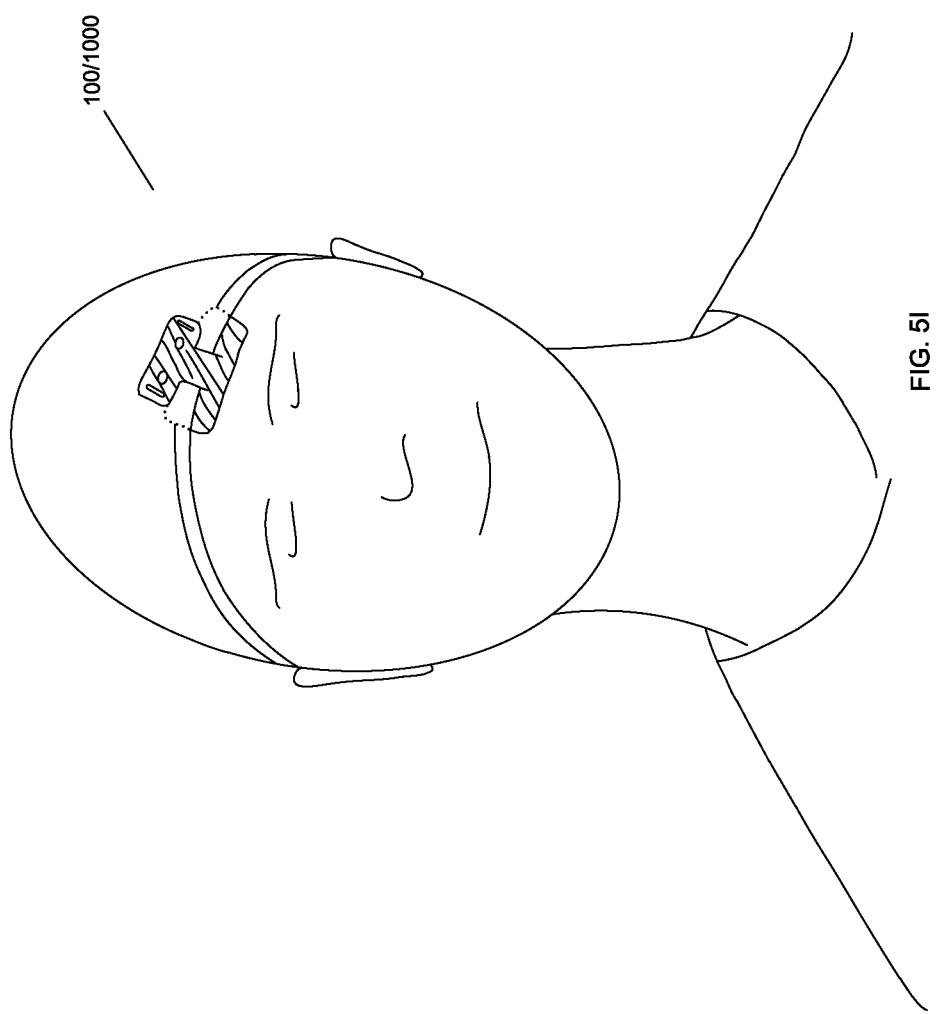
Figure 5K:
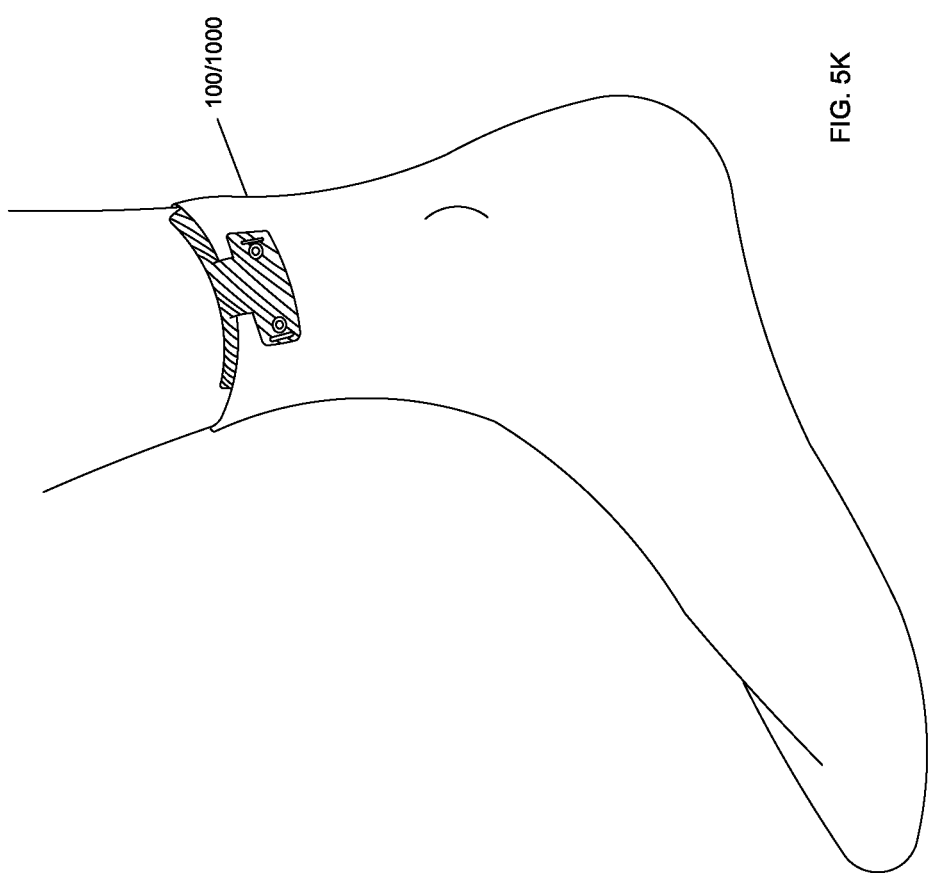

FIGS. 5A-5K are various embodiments of the sensor mount 100/1000 and/or sensor belt 110/1100 coupled to various articles of clothing and/or worn at various points on the body. The sensor mount 100/1000 may attach to and/or be integrated with articles of clothing and/or may be worn with the sensor belt 110/1100. The sensors 130 may be positioned on the inside of the sensor mount 100/1000 with respect to the wearer so that they may make contact with the wearer's skin. The electronics unit 140 may face outward from the wearer. Thus, the flexible substrate 120 and/or sensors 130 may contact the wearer comfortably, while the relatively less flexible electronics unit 140 may be positioned outward to prevent wearer discomfort. Specifically, FIG. 5A shows the sensor mount 100/1000 worn at the collar of a shirt, FIG. 5B shows the sensor belt 110/1100 around a wearer's waist, FIG. 5C shows the sensor belt 110/1100 around a wearer's torso, FIG. 5D shows the sensor mount 100/1000 worn at a waistband, FIG. 5E shows the sensor mount 100/1000 worn at the underband of a bra, FIG. 5F shows the sensor belt 110/1100 around a wearer's wrist, FIG. 5G shows the sensor mount 100/1000 worn at a cuff, FIG. 5H shows the sensor belt 110/1100 around a wearer's head, FIG. 5I shows the sensor mount 100/1000 worn at a headband or hatband, FIG. 5J shows the sensor belt 110/1100 around a wearer's ankle, and FIG. 5K shows the sensor mount 100/1000 worn at a sock band. These figures are intended as examples showing possible ways to wear the sensor mount 100/1000 and/or sensor belt 110/1100, although these articles may be worn at other places on the body.

Figure 6A:
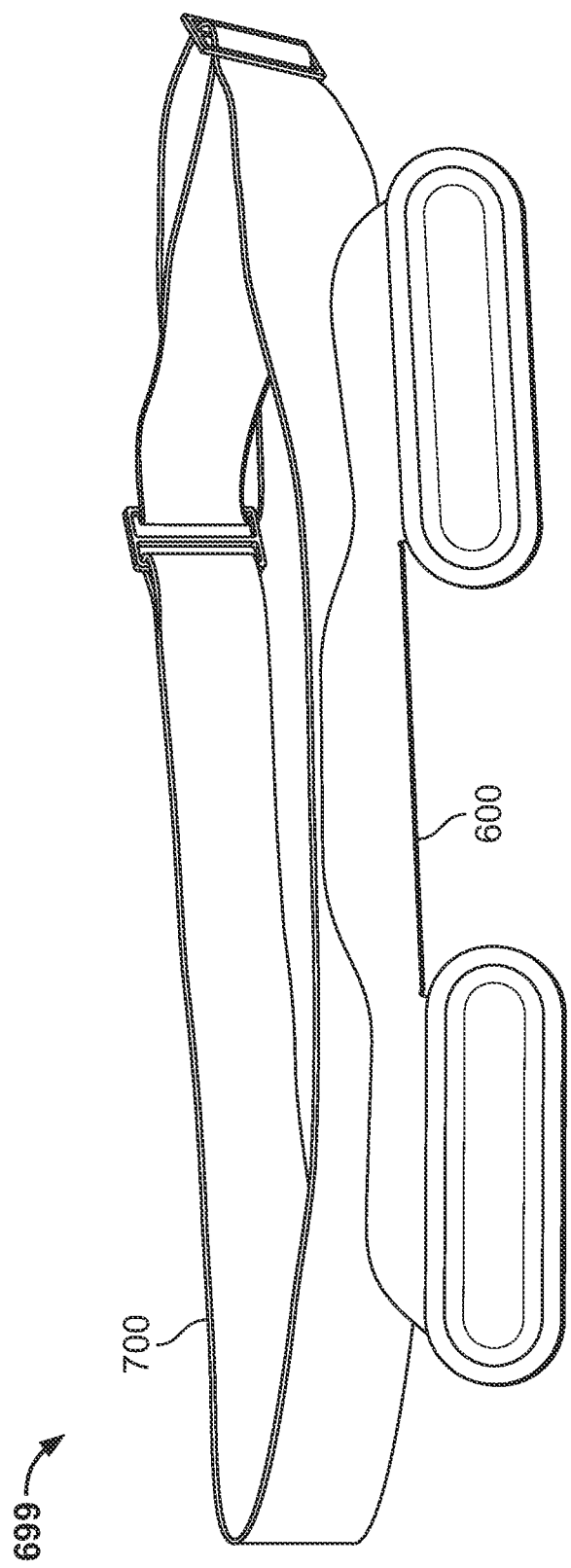
FIGS. 6A-6N illustrates an example sensing mechanism 699, according to an embodiment of the invention.
Figure 6K:
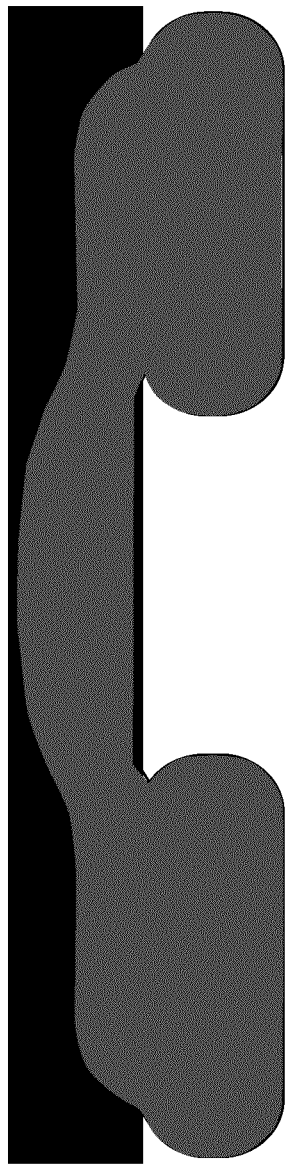
Figure 6L:
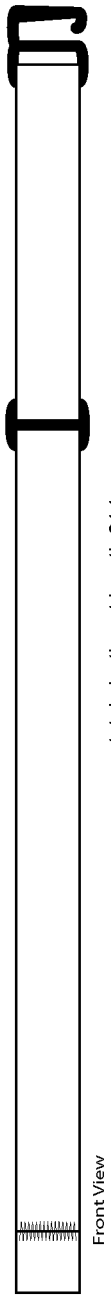
Figure 6M:
Figure 6N:
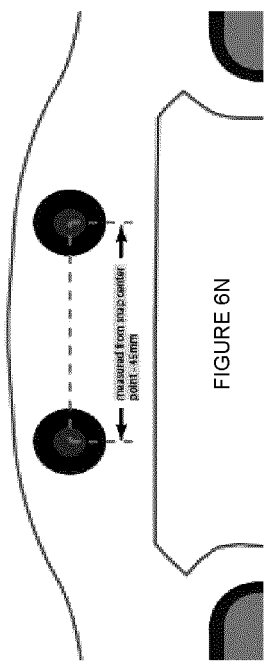

FIGS. 6A-6N illustrate a sensor mount according to an embodiment of the invention. FIG. 6A illustrates a perspective view of an example sensing mechanism 699, which includes an example sensor mount 600 and an example strap 700. FIG. 6B illustrates a front view of example sensor mount 600 wherein a sensor mechanism (not shown) comprises sensor substrates 605 used in conjunction with conductive snap buttons 620. FIG. 4 illustrates an example of a sensing mechanism (e.g., sensor circuit 300) that may be used in the embodiment shown in FIG. 6B. Those of ordinary skill will see that any or all components of sensor circuit 300 may be used in the embodiment shown in FIG. 6B.

FIG. 6C illustrates a back view of example sensor mount 600. FIG. 6D illustrates various fabrics and trims that may be used in some embodiments. (Note that only some of these may be used in some embodiments.) FIG. 6E illustrates a front view of an example strap 700 that may be used. FIG. 6F illustrates a back view of an example strap 700 that may be used. FIGS. 6E and 6F illustrates example connectors 710 that may be used to adjust and/or secure the strap 700. Many other types of connectors can be used. FIGS. 6E and 6F also illustrate example stitching (e.g., a bartack stitch) that may be done to secure the strap 700. Many other types of stitching can be used. FIG. 6G illustrates an example cut of fabric that may be used to make the sensor mount 600. FIG. 6H illustrates example glue that may be used to make the sensor mount 600. FIG. 6I illustrates example conductive fabric that may be used to make the sensors 605. FIG. 6J illustrates example material that may be used to secure the sensor (e.g., exo3900 EXOFLEX). FIGS. 6K, 6L, 6M and 6N illustrate various measurements that may be used in some embodiments of the invention.

While various embodiments have been described above, it should be understood that they have been presented by way of example and not limitation. It will be apparent to persons skilled in the relevant art(s) that various changes in form and detail can be made therein without departing from the spirit and scope. In fact, after reading the above description, it will be apparent to one skilled in the relevant art(s) how to implement alternative embodiments.

In addition, it should be understood that any figures which highlight the functionality and advantages are presented for example purposes only. The disclosed methodology and system are each sufficiently flexible and configurable such that they may be utilized in ways other than that shown.

Although the term "at least one" may often be used in the specification, claims and drawings, the terms "a", "an", "the", "said", etc. also signify "at least one" or "the at least one" in the specification, claims and drawings.

Finally, it is the applicant's intent that only claims that include the express language "means for" or "step for" be interpreted under 35 U.S.C. 112(f). Claims that do not expressly include the phrase "means for" or "step for" are not to be interpreted under 35 U.S.C. 112(f).

What is claimed is:

1. A sensor mount comprising:
   a flexible substrate folded to form a flexible inner portion arranged to face a wearer and a flexible outer portion arranged to face away from the wearer, the flexible inner portion and the flexible outer portion defining a channel and configured to secure the sensor mount to an article of clothing;
   a belt connected to the flexible outer portion, the outer flexible portion comprising two slits configured to receive the belt such that the belt is attachable to the outer flexible portion of the flexible substrate;
   a sensor disposed on the flexible inner portion of the flexible substrate;
   a conductor disposed in the flexible substrate and connected to the sensor;
   a joining portion connecting the flexible inner portion and the flexible outer portion; and
   an electronics unit in communication with the flexible outer portion of the flexible substrate and electrically coupled to the sensor via the conductor by the joining portion such that there is no electrical connection between the flexible inner portion and the flexible outer portion other than at the joining portion; and wherein the flexible inner portion of the flexible substrate is configured to flex independently of the flexible outer portion of the flexible substrate.

2. The sensor mount of claim 1, wherein the belt is configured to secure the sensor mount to a body of a wearer.

3. The sensor mount of claim 1, wherein the belt is configured to secure the sensor mount to a body of a wearer via a friction fit.

4. The sensor mount of claim 1, wherein the belt is configured to secure the sensor mount to a body of a wearer at a midsection or torso of the wearer.

5. The sensor mount of claim 1, wherein the belt comprises a molded material, a laminating material, or a combination thereof.

6. The sensor mount of claim 5, wherein the molded material comprises a synthetic rubber, silicon, PVC, or a combination thereof.

7. The sensor mount of claim 5, wherein the laminating material comprises a polymer, a knitted elastic, polypropylene, viscose, rayon, wool, cotton, silicon, or a combination thereof.

8. The sensor mount of claim 5, wherein the sensor mount is laminated to the laminating material.

9. The sensor mount of claim 1, wherein the article of clothing comprises a bra, a support top, a pair of shorts, a pair of pants, a sock or a shirt.

10. The sensor mount of claim 1, wherein the sensor comprises a heart rate sensor, a skin temperature sensor, a galvanic skin resistance sensor, an acceleration sensor, an optical sensor, an air temperature sensor, an air pressure sensor, a gyroscope, or any combination thereof.

11. The sensor mount of claim 1, wherein the flexible substrate comprises a knit or woven fabric, a nonwoven fabric, neoprene, an elastomeric film, or a combination thereof.

12. The sensor mount of claim 1, further comprising: a fastener configured to fasten the flexible inner portion to the flexible outer portion at a location apart from the joining portion.

13. The sensor mount of claim 1, wherein the electronics unit comprises an amplifier configured to amplify a sensor signal, an analog to digital converter configured to convert the sensor signal, a printed circuit board, a transceiver configured to send sensor data, a power supply, a microprocessor, or a combination thereof.

14. The sensor mount of claim 1, wherein the channel is configured to removably secure the sensor mount to the article of clothing.

15. The sensor mount of claim 1, further comprising one or more connectors positioned on the flexible outer portion of the flexible substrate to detachably connect the electronic unit to the flexible outer portion of the flexible substrate and to electrically connect the electronics unit with the conductor.

16. The sensor mount of claim 1 wherein the joining portion comprises a hinge.

* * * * *